United States Patent [19]
Trott

[11] Patent Number: 4,646,738
[45] Date of Patent: Mar. 3, 1987

[54] ROTARY SURGICAL TOOL
[75] Inventor: Arthur F. Trott, Largo, Fla.
[73] Assignee: Concept, Inc., Clearwater, Fla.
[21] Appl. No.: 804,898
[22] Filed: Dec. 5, 1985
[51] Int. Cl.⁴ ............................................. A61B 17/32
[52] U.S. Cl. .................................... 128/305; 128/752; 604/266
[58] Field of Search ............... 128/305, 751, 752, 755, 128/344; 604/22

[56] References Cited
U.S. PATENT DOCUMENTS

| 4,203,444 | 5/1980 | Bonnel et al. | 128/305 |
| 4,445,509 | 5/1984 | Auth | 128/305 |
| 4,466,429 | 8/1984 | Loscher et al. | 128/305 |

*Primary Examiner*—Henry Bennett
*Attorney, Agent, or Firm*—Frijouf, Rust and Pyle

[57] ABSTRACT

A rotatable surgical tool is disclosed for cutting and removing tissue from a patient. The tool includes an outer tubular member having a proximal end portion and a distal end portion. An inner tubular member has a distal end portion and a proximal end portion with the distal end portion of the inner tubular member having a cutter. The inner tubular member is rotatably disposed within the outer tubular member enabling the cutter to shear tissue disposed in the vicinity of the distal end portions upon rotation of the inner tubular member relative to the outer tubular member. A flexible transmission interconnects the distal end portion and the proximal end portion of the inner tubular member for transmitting rotational movement from a rotary power source to the cutter. The outer tubular member is constructed of a deformable material enabling the outer tubular member to be selectively bent, during fabrication of the tool, in a region adjacent the flexible transmission for facilitating the positioning of the cutter proximate the tissue of the patient. A vacuum source may be provided to be in fluid communication with the proximal end of the inner tubular member for removing tissue severed by the cutter.

21 Claims, 11 Drawing Figures

ROTARY SURGICAL TOOL

BACKGROUND OF THE INVENTION

1. Field of the Invention

This invention relates to a surgical tool for removing tissue from a patient. More specifically, this invention relates to a curved arthroscopic cutting device or the like.

2. Information Disclosure Statement

Until comparatively recently, most knee operations involved open surgery in order to remove growths on the patella or to remove torn cartilage from the knee joint. Such open surgery operations of necessity required a large incision thus requiring a considerable time to heal.

More recently, surgeons have been using closed surgery techniques which involve the use of an elongate rotary cutter which is inserted into a small incision of the patient adjacent the surgical site. The rotatable cutter includes an inner and an outer coaxial tube, the outer tube defining at the distal end thereof a cutter aperture or port which cooperates with a shearing blade secured to the distal end of the inner rotating tube. A source of partial vacuum is applied to the inner tube during use of the cutter in order to remove fluid and shaved particles from the surgical site.

Such closed surgery techniques have proved advantageous for a number of reasons. These advantages firstly apply to the patient undergoing such surgery because such closed surgery results in early ambulation or ability of the patient to walk after the operation. As a consequence, the patient has a shorter stay in hospital and is therefore able, to return to daily activities at an earlier date. Furthermore, by performing closed surgery, post-operative discomfort and stiffness due to the operation is substantially reduced. Finally, because closed surgery does not require an extensive longitudinal incision, scarring is kept to a minimum.

Advantages afforded to the surgeon, by such closed surgery techniques include being more readily accepted by the patient because of the reduced trauma experienced by the patient undergoing such closed surgery. Furthermore, the surgeon is able to perform a wide range of operative procedures utilizing the aforementioned arthroscopic techniques. Such operative procedures include intra-articular surgery as described hereinbefore for removing loose tissues from within the knee joint. Additionally, such procedures permit removal of pathological plica, and removal of chondromalacia of the patella. Other procedures include removal of torn meniscus or synovitis. In addition to the wide range of operative procedures that may be performed by a surgeon using such closed surgery techniques, the surgeon also experiences a reduction in the requirement for post-operative management as patients do not require sutures to be removed as is the case with open surgery.

With regard to the functioning of a hospital, the aforementioned closed surgical technique results in an increase in the possibility of treating patients requiring knee surgery as out-patients rather than requiring such a patient to occupy a hospital bed as was the case with open surgery. Therefore, viewed from the aspect of hospital management, closed surgery techniques result in an increase in revenue and a reduction in the stay of the patient in the hospital.

U.S. Pat. No. 4,203,444 to Bonnell et al discloses a surgical instrument of the aforementioned type suitable for performing closed surgery of the knee. The closed surgery technique as taught by Bonnell et al includes administering to the patient a local anesthetic followed by perforating the outer skin of the patient at selected points about the knee joint by means of trocar cannula. A liquid is introduced from a liquid source into one of the cannula to inflate the knee joint pouch. The joint is illuminated and observed by means of fibroptic probe means introduced through another cannula such that the knee joint may be visualized by the surgeon by means of close-circuit television equipment. The distal end of the arthroscopic rotary surgical cutting tool is then inserted through a further cannula and manipulated by the surgeon into the vicinity of the tissue. As the rotary blade rotates in the vicinity of the tissue to be removed, the surgeon is able to observe the removal of tissue by means of a television monitor. Furthermore, tissue formations cut or shaved away by the rotary surgical cutting tool are removed from the surgical site through the inner rotating tube of the rotary surgical cutting tool by means of a partial vacuum. Bonnell et al also describes how the surgeon manipulates the patella of the patient and manipulates the instrument backwards and forwards in order to position the cutting element at the desired angle relative to the surgical site. Bonnell et al also teaches that the direction of rotation of the blade may be reversed by suitable control means operated by the surgeon.

While the aforementioned surgical instrument has been very successful in enabling closed surgery to be preformed on patients, certain problems have been experienced by surgeons utilizing the aforementioned arthroscopic tools. One of the main problems has been that the surface of the patella to be treated is not planar. Therefore, although as disclosed in U.S. Pat. No. 4,203,444 the tool can be moved axially and back and forth, such maneuvers have presented difficulties when attempting to correctly position the cutting element relative the site to be planed. As stated in U.S. Pat. No. 4,203,444, the surgeon during the arthroscopic surgery is required to move the patella of the patient. However, the patella will only move to a limited degree thus inhibiting the surgical technique. Accordingly, there has existed in the art, the need for a cutter that could be variably positioned relative to a curved surface to be treated without the need for removing the tool and reinserting the same within a further cannula disposed angularly relative to the first cannula.

The prior art has also utilized rotary surgical cutting means in the form of a rotary burr cutting means. The rotary burr cutting means was disposed on a distal end of an inner rotating member which inner rotating member was disposed in an outer tubular member. The rotary burr cutting means functioned to smooth cut tissue during an arthroscopic surgical operation.

The present invention has as a primary objective the provision of a surgical tool that overcomes the aforementioned inadequacies of the prior art devices and provides an improvement which is a significant contribution to the advancement of the closed surgery art.

The present invention overcomes the aforementioned problem and inadequacy of the prior art device by providing a rotary surgical tool having an outer tube which may be bent during manufacture such that the cutting element may be positioned at various desired angle relative to the surface of the patella.

Another object of the present invention is the provision of a surgical tool including an inner tubular member having a flexible transmission disposed within an outer tubular member, wherein the outer tubular member may be bent during manufacture to a desired configuration.

Another object of the present invention is the provision of a surgical tool having a flexible transmission which defines a channel for removing cut tissue by means of a source of partial vacuum.

Another object of the present invention is the provision of a surgical tool having a flexible transmission which includes a spirally wound tube.

Another object of the present invention is the provision of a surgical tool having a flexible transmission interposed in an inner tubular member for transmitting rotary movement of a motor to a cutting means. The flexible transmission includes a plurality of coaxial spirals of strip material, each spiral being disposed angularly relative to an adjacent spiral such that the spirally wound tube not only mechanically transmits rotational movement of the drive motor to the cutting means, but also provides a substantially fluid tight conduit for the removal of particles of tissue removed from the surgical site.

Another object of the present invention is the provision of a surgical tool having an outer tubular member for the reception therein of an inner tubular member having a flexible transmission means. The outer tubular member is of a deformable material having sufficient mechanical strength to enable insertion of the distal end of the outer tubular member into the incision towards the surgical site.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The invention is defined by the appended claims with a specific embodiment shown in the attached drawing. For the purpose of summarizing the invention, the invention is incorporated into an apparatus and a method of making a surgical tool comprising an outer tubular member having a proximal end portion and a distal end portion. An inner tubular member includes a proximal end portion and a distal end portion with the distal end portion of the inner tubular member having cutting means. The inner tubular member is rotatably disposed within the outer tubular member. Means are provided for connecting the proximal end portion of the inner tubular member to a source of rotary power enabling the cutting means to cut tissue of a patient upon rotation of the inner tubular member relative to the outer tubular member. A flexible transmission interconnects the distal end portion and the proximal end portion of the inner tubular member for transmitting rotational movement from the rotary power source to the cutting means. The outer tubular member is constructed of a rigid and deformable material enabling the outer tubular member to be selectively bent during fabrication in a region adjacent the flexible transmission during fabrication of the tool for facilitating the positioning the cutting means proximate the tissue of the patient. Once bent, the outer tubular member retains the selective bent configuration. A vacuum source may be provided to be in fluid communication with the distal end of the inner tubular member for removing tissue severed by the cutting means.

In a more particular embodiment of the invention, the invention relates to a motor-driven, hand-held surgical tool and the method of making the same for removing tissue from a patient. The tool comprises an outer tubular member wherein the distal end portion of the outer tubular member defines an outer cutting aperture. The cutting means or cutter is rotatably disposed within the outer tubular member adjacent to the outer cutting aperture and preferably comprises an inner cutting aperture disposed in the distal end portion of the inner member. The inner cutting aperture cooperates with the outer cutting aperture such that rotation of the inner tubular member within the outer tubular member enables tissue disposed in the vicinity of the outer cutting aperture to be sheared by the interaction of the inner cutting aperture with the outer cutting aperture. The flexible transmission is connected to the cutter and extends through the outer tubular member towards the motor. The flexible transmission transmits rotational movement of the motor to the cutter enabling the outer tubular member to be selectively bent between the distal end portion and proximal end portion of the outer tubular member for positioning the outer cutting aperture adjacent to the tissue to be removed.

More specifically, the outer tubular member is of stainless steel and defines a bore for the reception therein of the rotary cutter and flexible transmission means. The bore has a uniform cross-sectional area throughout the length thereof, thereby permitting the rotary cutter and flexible transmission means to be inserted and removed from the proximal end portion of the outer tubular member *prior* to bending of the outer tubular member during fabrication of the surgical tool. The flexible transmission means includes an inner spiral of strip material which defines a first channel such that the first channel extends along the length of the inner spiral. The flexible transmission means comprises three spirally wound tubes of flat metallic ribbon such as stainless steel. The three layers are of such diameters that sliding contact with a minimum of radial clearance, exists between adjacent surfaces.

The inner, middle and outer spirals are wound in alternating opposite directions and spot welded at each end to form a composite flexible tube.

Torque applied to one end of the assembly will be transmitted by alternate layers trying to expand or unwind or trying to contract or wind up. The middle spiral will either attempt to expand and be resisted by the contraction of the outer layer or the middle spiral will attempt to contract or wind up and be resisted by the inner spiral.

The three spirals thereby form a spirally wound tube with the three spirals being welded to each other by spot welds disposed longitudinally along the spirally wound tube to provide a flexible transmission bidirectional (clockwise and counter-clockwise) means defining a channel for the passage therethrough of tissue removed by the rotary cutter.

The inner tubular member includes the distal end portion and the proximal end portion with the flexible transmission means interposed therebetween. The rotary cutter is defined by the inner distal end portion. Preferably, the outer spiral is of a shorter length than the middle and inner spirals thereby defining a first and a second ledge disposed adjacent the first and second ends of the spirally wound tube. The first ledge receivably cooperates with the distal end portion whereas the second ledge receivably cooperates with the proximal end portion such that rotary movement of the motor is flexibly transmitted to the rotary cutter in either a clockwise or counter-clockwise direction. This enables the cutter to be rotated in the same direction relative the tissue being cut notwithstanding the movement of the cutter from one position on the patella to another position opposite the first position.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art the such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION

Figure 1:
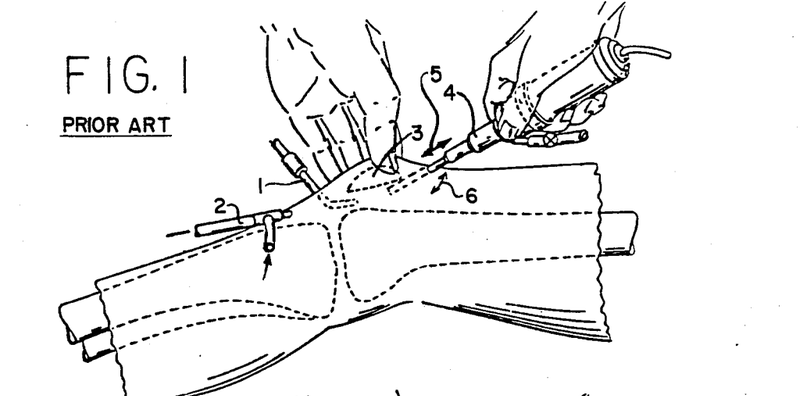
FIG. 1 is a diagrammatic view showing the general method of performing closed surgery on a knee cap of a patient using a prior art surgical cutter.

FIG. 1 is a diagrammatic view of prior art closed surgery being performed on the knee joint of a patient and includes a fluid introducing cannula 1. A fibroptic illuminating and display system 2 is shown inserted adjacent to the surgical site shown as the patella 3 of the patient. A prior art surgical cutter 4 is moveable axially relative to the patella 3 as indicated by the arrow 5 and from one side to the other as indicated by the arrow 6. This prior art surgical technique requires the manipulation of the patella 3 as heretofore described.

Figure 2:
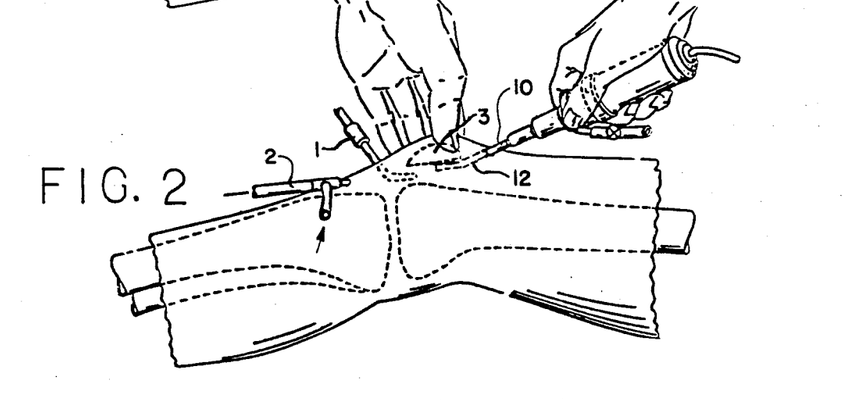
FIG. 2 is a similar view to that shown in FIG. 1 but shows the same closed surgery being performed using a surgical cutter according to the present invention with the outer tube bent upwardly to faciliate treatment of the patella.

FIG. 2 is a similar view to that shown in FIG. 1 but shows a surgical cutter generally designated 10 according to the present invention in which an outer tubular member 12 of the surgical tool 10 is bent upwardly to facilitate placement of the surgical tool 10 adjacent to the surgical site.

Figures 3, 4, 5, 6, 8:
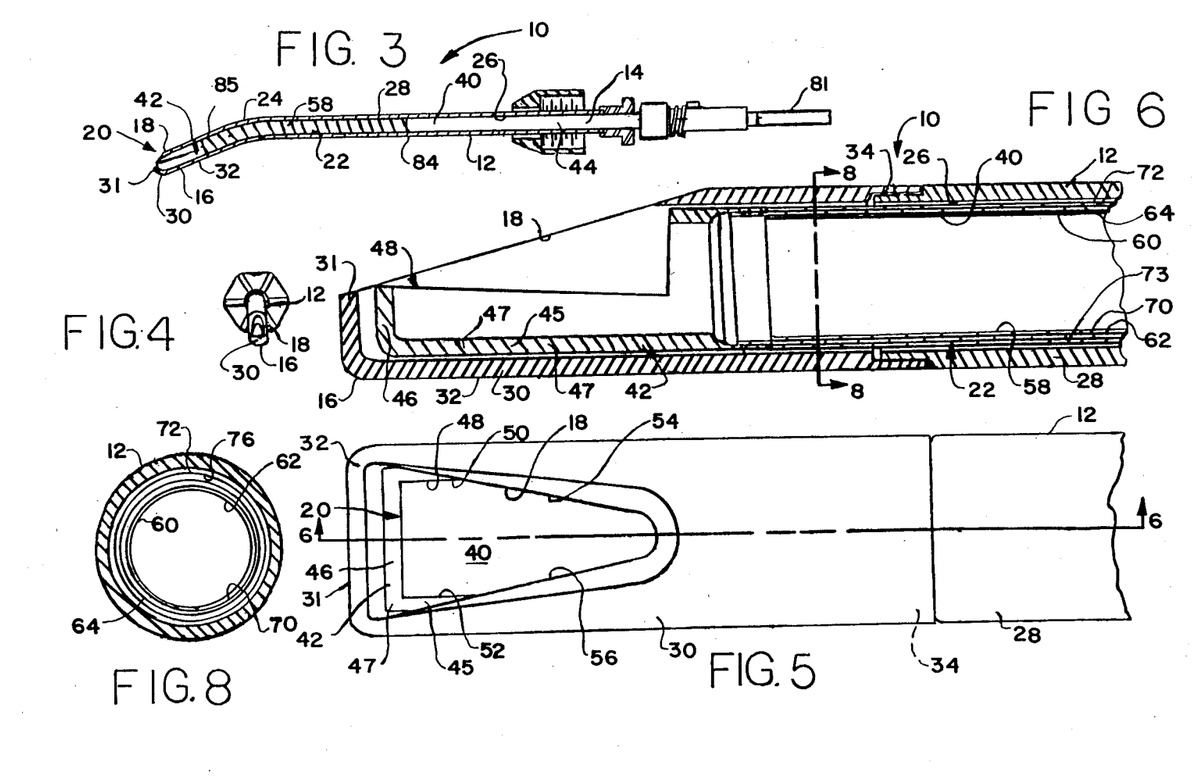
FIG. 3 is a sectional view of the surgical cutter of the present invention with the outer tube being bent downwardly.
FIG. 4 is a left end view of the surgical cutter shown in FIG. 3.
FIG. 5 is an enlarged plan view of the distal end portion of the surgical cutter shown in FIG. 3.
FIG. 6 is a sectional view taken on the line 6—6 of FIG. 5.
FIG. 8 is a sectional view taken on the line 8—8 of FIG. 6.

FIG. 3 is a sectional view of the motor-driven, hand-held surgical tool 10 shown in FIG. 2. The surgical tool 10 includes the outer tubular member 12 having a proximal end portion 14 and a distal end portion 16. A tissue cutting means generally designated 20 is rotatably disposed within the outer tubular member 12. In this embodiment, the cutting means 20 includes an outer cutting aperture 18 in the outer tubular member 12 such that rotation of the cutting means 20 within the distal end portion 16 of the outer tubular member 12 enables tissue disposed in the vicinity of the outer cutting aperture 18 to be sheared by the interaction of the cutting means 20 with the outer cutting aperture 18. A flexible transmission means, generally designated 22 to be described in more detail hereinafter, is connected to the cutting means 20 and is disposed within the outer tubular member 12. The flexible transmission means 22 transmits rotational movement from a motor (not shown) to the cutting means 20 enabling the outer tubular member 12 to be selectively bent during the fabrication of the tool at 24 between the distal end portion 16 and the proximal end portion 14 of the outer tubular member 12 for positioning the outer cutting aperture 18 adjacent to the surgical site. The outer tubular member 12 is of a material which when bent at 24 retains the bent configuration. An example of a suitable material for use in the fabrication of the outer tubular member 12 is stainless steel. The outer tubular member 12 defines a bore 26 for rotatably receiving therein the cutting means 20 and the flexible transmission means 22. The bore 26 is dimensioned such that the cutting means 20 and the flexible transmission means 22 may be inserted and removed from the outer tubular member 12 through the proximal end portion 14 of the outer tubular member 12. The outer tubular member 12 also includes an intermediate portion 28 shown in FIGS. 5 and 6 extending between the proximal end portion 14 and the distal end portion 16. The distal end portion 16 is shown as a partial cylinder 30 having a cylindrical end 31 defining an outer cap 32. The open end 34 of the outer cap 32 is rigidly secured by soldering or the like to the intermediate portion 28. The outer cutting aperture 18 is defined by the outer cap 32.

The tissue cutting means 20 shown in FIGS. 3, 5 and 6 is an inner tubular member 40 having an inner distal end portion 42 and an inner proximal end portion 44 with the flexible transmission means 22 interposed therebetween. The inner distal end portion 42 is shown as a cylinder 45 having a cylindrical end 46 defining an inner cap 47. The inner cap 47 defines an inner cutting aperture 48 such that at least a portion of edges 50 and 52 of the inner cutting aperture 48 are machine sharpened for coacting with edges 54 and 56 of the outer cutting aperture 18 as shown in FIG. 6 for shearing tissue to be removed from the patient. The inner cap 47 has an external diameter which is less than the internal diameter of the outer cap 32 of the outer tubular member 12 such that the inner cap 47 freely rotates or is journaled within the outer cap 32 permitting at least a portion of the edges 50 and 52 of the inner cutting aperture 48 to coact with edges 54 and 56 of the outer cutting aperture 18 to thereby sever tissue when rotated in either a clockwise or counter-clockwise direction.

Figure 7:
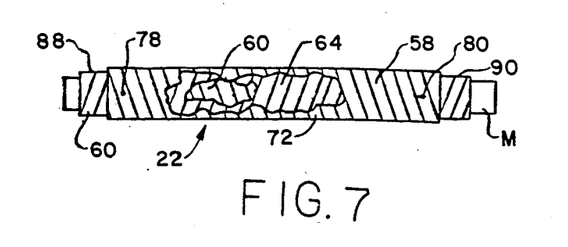
FIG. 7 is an enlarged side elevational view partially in section of the spirally wound tube of the flexible transmission means of the present invention.

The flexible transmission means 22 is shown generally in FIGS. 3 and 5 and is shown more particularly with reference to FIGS. 7 and 8. The flexible transmission means 22 includes a composite spirally wound tube 58. The spirally wound tube 58 includes an inner spiral 60 shown in FIGS. 6, 7 and 8. The inner spiral 60 is of strip material such as flat stainless steel ribbon and is wound upon a suitable mandrel M as shown in FIG. 7 such that the inner spiral 60 defines a first channel 62 shown in FIGS. 6 and 8. A middle spiral 64 of flat stainless steel strip material is shown in FIGS. 6, 7 and 8. The middle spiral 64 is oppositely wound relative to inner spiral 60 such that the middle spiral 64 is disposed angularly relative to the inner spiral 60 as shown in FIG. 7. The middle spiral 64 defines a second channel 70 shown in FIG. 8 having a diameter slightly greater than the external diameter of the inner spiral 60 such that the inner spiral 60 is slidably disposed within and in close proximity to the middle spiral 64. An outer spiral 72 is of flat stainless steel strip oppositely wound relative the middle spiral 64 so that the outer spiral 72 is material as shown in FIGS. 6, 7 and 8. The outer spiral 72 is disposed opposite or angularly relative to the middle spiral 64. The angle of the outer spiral 72 may be approximately the same as the angle of the inner spiral 60. The outer spiral 72 defines a third channel 76 shown in FIG. 8 such that the third channel 76 has a slightly greater diameter than the external diameter of the middle spiral 64. The middle spiral 64 is slidably disposed within and in close proximity to the outer spiral 72. The three spirals, 60, 64 and 72 are of such diameters that sliding contact, with a minimum of radial clearance, exists between adjacent spiral surfaces.

As shown more particularly with reference to FIG. 7, a first fastening means 78 which may be a spot-weld, is disposed near one end of the composite spirally wound tube 58. The spot-weld 78 unites together all three of the spirals 60, 64 and 72. A second fastening means 80 which is spaced longitudinally relative to the first fastening means 78 includes a spot-weld, which welds together the inner, middle and outer spirals 60, 64 and 72 respectively. The spot welding holds and supports the three spirals axially relative to each other to form the spirally wound tube 58 to permit transmission of rotary movement from a source of rotary motion such as a motor connected to the inner proximal end portion 44 through a coupling generally designated 81 to convey tissue removed by the cutting means 20 through the first channel 62 defined by the spirally wound tube 58.

The flexible transmission means 22 is connected to the inner proximal end portion 44 of the inner tubular member 40 at 84 with the inner tubular member 40 being in fluid tight communication with the first channel 62 of the spirally wound tube 58 and is disposed adjacent to the second fastening means 80. The flexible transmission means 22 is also connected in a fluid tight communication with the inner cap 47 at 85. The coupling 81 of the proximal end portion 44 is in fluid communication with a source or partial vacuum (not shown) such that tissue removed from the patient during rotation of the cutting means 20 enters through suction port or aperture 21 and is drawn through the first channel 62 and through the proximal end portion 44 towards the coupling 81. Furthermore, the coupling 81 provides rotary motion to the cutter 20 from a source of rotary power (not shown).

As shown more particularly in FIG. 7, the outer spiral 72 is shorter than the inner and middle spirals 60 and 64 such that a first ledge 88 is defined by spirals 60 and 64 adjacent to the first fastening means 78. A second ledge 90 is defined by the spirals 60 and 64 in the vicinity of the second fastening means 80. The first ledge 88 cooperates with the inner diameter of the inner cap 47 such that the inner cap 47 may be soldered or welded or otherwise secured to the spiral wound tube 58 adjacent to the first ledge 88. Similarly, the inner diameter of the inner proximal end portion 44 cooperates with the second ledge 90 and is soldered, welded, or otherwise secured to 82 to the spiral wound tube 58.

Figure 9:
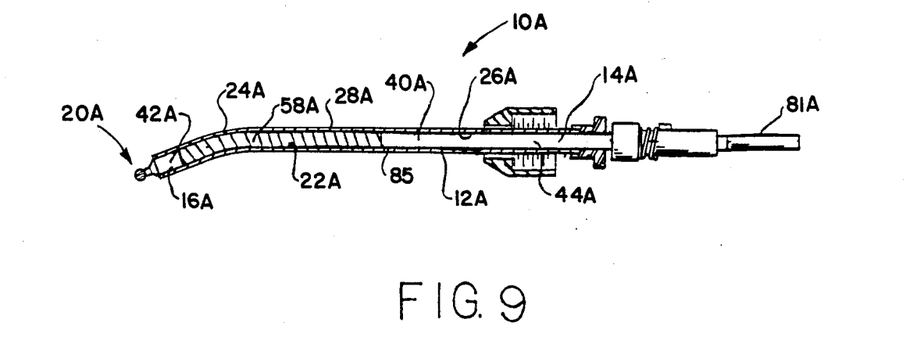
FIG. 9 is an elevational view of a second embodiment of the present invention illustrating a surgical cutter incorporating a rotary burr cutting means.

The surgical tool of the present invention essentially includes an outer tubular member 12, an inner tubular member 40, a flexible transmission means 22 and a rotary cutter 20. The present apparatus invention may be modified or incorporated into various alternative designed rotary tools. FIG. 9 is a sectional view of the surgical tool 10A including an outer tubular member 12A having a proximal end portion 14A and a distal end portion 16A. A rotary burr cutting means 20A is mounted on the distal end portion 42A of the inner tubular member 40A. The inner tubular member 40A is rotatably disposed within the outer tubular member 12A. The flexible transmission means 22A transmits rotational movement from the motor (not shown) to the burr cutting means 20A and enables the outer tubular member 12A to be selectively bent at 24A between the distal end portion 16A and the proximal end portion 14A of the outer tubular member 12A. The flexible transmission means 22A further provides a channel 61 within the spirally wound tube 58 in fluid communication with a vacuum source (not shown) to convey tissue removed from the patient by rotary burr cutting means 20A and entering through suction port 21A. The rotary tool 10A incorporating the cutting burr 20A operates in a manner similar to the cutting tool 10 heretofore described.

A method of making the spirally wound tube 58 includes the steps of first winding the three springs or spirals 60, 64 and 72 and cutting to length. The spirals are then assembled over a mandrel M as shown in FIG. 7. Preferably, the inner spring is a right-hand spiral, the middle spring is a left-hand spiral, and the outer spring is a right-hand spiral. Using this construction, when torque is applied in a right-hand direction, the inner coil tries to expand but the middle coil constrains it as it tries to collapse. When torque is applied in a left-hand direction, the outer coils oppose themselves similarly. The spirals 60, 64 and 72 are spot welded together at 78 and 80 to provide the composite spirally wound tube 58. The mandrel M is removed from the first channel 62 defined by the inner spiral 60 and the inner distal end portion 42 is secured to the first ledge 88 of the spirally wound tube 58. The inner proximal end portion 44 is secured to the second ledge 90 of the spirally wound tube 58 to form the inner tubular member 40. The flexible transmission provides both rotational communication and fluid communication between the inner distal end portion 42 and at the inner proximal end portion 44. The inner tubular member 40 is inserted within the outer tubular member 12 through the outer proximal end portion 14.

In operation and use of the rotary surgical tool as described hereinbefore, a local anesthetic is administered in the region of the knee joint of the patient. A sharp trocar is inserted through the skin of the patient adjacent to the knee cap or patella of the patient. The trocar cannula is connected to a source of infusion such that as liquid is infused into the knee joint, synovial tissue is rendered mobile by the inflating liquid so that the synovial tissue becomes displaced and floats within the infused liquid. A further trocar cannula is inserted in the vicinity of the first cannula and a fibroptic probe connected to a television camera and monitor is positioned to both illuminate and display the surgical site thereby enabling the surgeon to correctly position the rotary hand-held surgical tool to be subsequently inserted within the knee of the patient. A very small incision is then made by the surgeon to permit insertion of the distal end of the rotary surgical tool within the incision. The distal end 16 of the surgical tool in then gently urged inwardly through the incision and towards the vicinity of the surgical site until the outer distal end portion 16 of the tool becomes visible to the surgeon by means of the monitor. When the outer cutting aperture 18 comes into the view of the surgeon by means of the monitor, the outer cutting aperture 18 may be correctly positioned relative to the surgical site by virtue of the curved configuration of the outer tubular member 12. This curved configuration of the outer tubular member 12 greatly facilitates the correct positioning of the cutter means relative to the tissue to be removed, especially where the surgical site is disposed at a point where only limited access is available.

Figure 10:
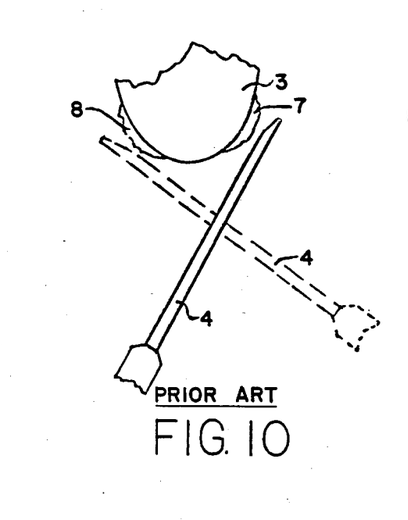
FIG. 10 is a diagrammatic representation of a prior art surgical cutter being used for treating different portions of a curved surface at a surgical site.

More particularly, with use of the prior art devices as shown in FIG. 10, when a surgeon wished to treat one portion 7 of a curved surgical site 3 and subsequently to treat a further portion 8 of the surgical site, the surgeon using a straight prior art surgical cutter 4 found it necessary to insert the surgical cutter 4 at two angularly disposed dispositions relative to the surgical site 3. The second of these positions is shown in phantom outline in FIG. 10. Not only does this second positioning of the cutter 4 require a second incision with the attendant additional operation time, but additionally such subsequently positioning of the cutter means 4 results in additional scarring of the patient.

Figure 11:
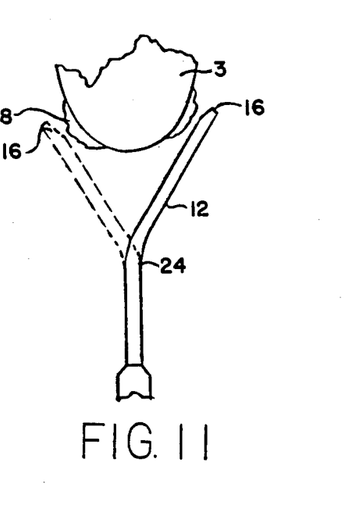
FIG. 11 is a diagrammatic representation similar to that shown in FIG. 10 but showing the different portions of the curved surface being treated with a surgical tool according to the present invention.

According to the present invention as shown in FIG. 11, the portions 7 and 8 of the surgical site 3 to be treated are able to be treated by the bent surgical tool 10 of the present invention without removing the tubular member 12 from the surgical site 3. In operation of the tool according to the present invention when the surgeon has completed the treatment of the portion 7, the outer distal end portion 16 of the tubular member 12 is repositioned as shown in phantom outline in FIG. 11 such that the outer distal end portion 16 is disposed adjacent to the second portion 8 to be treated without removing the surgical tool 10 relative the surgical site 3. Such repositioning of the distal end 16 is accomplished by rotating the outer tubular member 12 relative to the surgical site 3 resulting in the repositioning and correct positioning of the rotary cutter relative to the surface to be treated by virtue of the bend 24 in the elongate tubular member 12. If desired, the rotational direction of the cutter may be reversed to enable the cutter to rotate in the same direction relative the tissue being cut.

The curved rotary type cutter of the present invention provides a significant improvement over the prior art devices particularly when treating areas that are difficult to access. Also the cutter may be positioned at the correct angular disposition relative to the surgical site even when the surgical site presents a curved surface to be treated. Furthermore, the outer tubular member in cooperation with the flexible transmission means permits bending of the outer tubular member in almost any direction relative to the rigid tubular portion. This bending is facilitated particularly in view of the spiral wound tube which not only transmits rotary movement of the motor to the cutting means but also provides a substantially fluid tight channel for the removal of tissue from the surgical site.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A surgical tool for cutting tissue from a patient upon rotation by a rotary power source, comprising:
   an outer tubular member having a proximal end portion and a distal end portion;
   an inner tubular member having a proximal end portion and a distal end portion;
   said distal end portion of said inner tubular member having a cutting means;
   said inner tubular member being rotatably disposed within said outer tubular member;
   means connecting said proximal end portion of said inner tubular member to a source of rotary power enabling said cutting means to cut the tissue of a patient upon rotation of said inner tubular member relative to said outer tubular member;
   a flexible transmission means interposed between said distal end portion and said proximal end portion of said inner tubular member for transmitting rotational movement from the rotary power source to said cutting means;
   said flexible transmission means including a plurality of coaxial spirally wound layers being wound in alternating opposite direction relative to each other to enable rotation of said cutting means in either a clockwise or counter-clockwise direction; and
   said outer tubular member being of a deformable material enabling said outer tubular member to be selectively bent in a region adjacent said flexible transmission for facilitating said positioning of said cutting means proximate the tissue of the patient.

2. A surgical tool as set forth in claim 1, including means connecting said proximal end of said inner tubular member to be in fluid communication with a vacuum source for removing tissue severed by said cutting means.

3. A surgical tool as set forth in claim 1, wherein said tissue cutting means disposed at said distal end portion of said inner tubular member further includes:
   a first and second cutting edge to enable tissue to be cut when said tissue cutting means rotates in a clockwise or counter-clockwise direction.

4. A surgical tool as set forth in claim 1, wherein said flexible transmission means is a spirally wound tubing means comprising:
   an inner spiral of strip material being wound between said distal end portion and said proximal end portion of said inner tubular member;
   a middle spiral of strip material being wound between said distal end portion and said proximal end portion of said inner tubular member;
   an outer spiral of strip material being wound between said distal end portion and said proximal end portion of said inner tubular member;
   fastening means for securing said inner, middle and outer spiral of strip material to said distal end portion and said proximal end portion of said inner tubular member; and
   said inner, middle and outer spirals being oppositely wound relative to each other for providing a cooperating flexible mechanical coupling while simultaneously defining an inner spiral bore for conveying tissue removed from the patient from said distal end portion to said proximal end portion of said inner tubular member.

5. A surgical tool for cutting tissue from a patient upon rotation by a rotary power source, comprising:
   an outer tubular member having a proximal end portion and a distal end portion;
   said distal end portion of said outer tubular member defining an outer aperture;
   an inner tubular member having a proximal end portion and a distal end portion;
   said distal end portion of said inner tubular member defining an inner aperture;
   said inner tubular member being rotatably disposed within said outer tubular member;
   means connecting said proximal end portion of said inner tubular member to the rotary power source enabling said inner and outer apertures to cut the tissue of the patient upon rotation of said inner tubular member relative to said outer tubular member;
   flexible transmission means interposed between said distal end portion of said inner tubular member and said proximal end portion of said inner tubular member for transmitting rotational movement of the rotary power source to said inner aperture;
   said flexible transmission means including a plurality of coaxial spirally wound layers being wound in alternating opposite direction relative to each other to enable rotation of said cutting means in either a clockwise or counter-clockwise direction; and
   said outer tubular member being of a deformable material for enabling said outer tubular member to be selectively bent in a region proximal said flexible transmission means for facilitating the positioning said inner and outer apertures proximate the tissue to be cut of the patient.

6. A surgical tool as set forth in claim 5, wherein said deformable material of said outer tubular member is stainless steel.

7. A surgical tool as set forth in claim 5, wherein said outer tubular member defines an internal bore for rotatably receiving therein said inner tubular member and said flexible transmission means.

8. A surgical tool as set forth in claim 7, wherein said internal bore is of uniform cross-sectional area along the length of said outer tubular member.

9. A surgical tool as set forth in claim 5, wherein said distal end portion said outer tubular member comprises an outer cap portion defining said outer aperture; and
   means connecting said outer cap portion to said proximal end portion of said outer tubular member.

10. A surgical tool as set forth in claim 5, wherein said distal end portion of said inner tubular member comprises an inner cap portion defining said inner aperture; and
    said flexible transmission means interconnecting said inner cap portion and said proximal end portion of said inner tubular member.

11. A surgical tool as set forth in claim 10, wherein said outer cap portion is of a hollow cylindrical configuration having one cylindrical end thereof being closed by an outer cap wall; and
    said inner cap portion being of a hollow cylindrical configuration and having one cylindrical end thereof being closed by an inner cap wall.

12. A surgical tool as set forth in claim 11, wherein at least a portion of an edge of said outer aperture of said outer tubular member is sharpened; and
    at least a portion of an edge of said inner aperture of said inner tubular member being sharpened for coacting with said sharpened edge of said outer aperture for shearing the tissue of the patient upon said inner tubular member rotating within said outer tubular member.

13. A surgical tool as set forth in claim 12, wherein said inner cap portion of said inner tubular member has an external diameter which is less than the internal diameter of said outer cap portion of said outer tubular member for enabling said inner cap portion to rotate within said outer cap portion to permit said sharpened edge of said inner aperture to coact with said sharpened edge of said outer aperture as said inner tubular member rotates within said outer tubular member.

14. A surgical tool as set forth in claim 5, wherein said flexible transmission means comprises:
    an inner spiral of strip material being wound between said distal end portion and said proximal end portion of said inner tubular member;
    a middle or center spirally wound strip material being wound between said distal end portion and said proximal end portion of said inner tubular member;
    an outer spiral of strip material being wound between said distal end portion and said proximal end portion of said inner tubular member;
    fastening means for securing said inner and outer spiral of strip material to said distal end portion and said proximal end portion of said inner tubular member; and
    said inner and outer spirals being oppositely wound relative to each other for providing a cooperating flexible mechanical coupling while simultaneously defining an inner spiral bore for conveying tissue removed from the patient from said distal end portion to said proximal end portion of said inner tubular member.

15. A surgical tool as set forth in claim 5, wherein said flexible transmission means further includes:
an inner spiral of strip material defining an inner spiral bore extending through and along the length of said inner spiral;
said inner spiral of strip material being wound in a first direction between said distal end portion and said proximal end portion of said inner tubular member;
a middle spiral of strip material defining a middle spiral bore extending through and along the length of said middle spiral ;
said middle spiral bore of said middle spiral having a greater diameter than the external diameter of said inner spiral enabling said inner spiral to be slidably disposed within and in close proximity to said middle spiral;
said middle spiral of strip material being wound in a second direction between said distal end portion and said proximal end portion of said inner tubular member;
an outer spiral of strip material defining a outer spiral bore extending through and along the length of said outer spiral;
said outer sprial bore having a greater diameter than the external diameter of said middle spiral enabling said middle spiral to be slidably disposed within and in close proximity to said outer spiral;
said outer spiral of strip material being wound in a first direction between said distal end portion and said proximal end portion of said inner tubular member;
fastening means for securing said inner, middle and outer spirals of strip material to said distal end portion and said proximal end portion of said inner tubular member; and
said first direction being angularly disposed relative to said second direction for fastening said inner, middle and outer spirals into a cooperating flexible coupling while simultaneously defining said inner spiral bore for conveying tissue removed from the patient from said distal end portion to said proximal end portion of said inner tubular member.

16. A surgical tool as set forth in claim 13, wherein said fastening means are spot welds which weld adjacent portions of said spirals together to provide a three-ply composite flexible spirally wound tubing.

17. A surgical tool as set forth in claim 16, wherein each of said spiral strip materials is bias by a resiliency in said spiral material; and
said bias of said inner and outer spirals being substantially the same direction and angularly disposed relative to said bias of said middle spiral.

18. A surgical tool as set forth in claim 17, wherein said inner tubular member further includes:
said proximal end portion being substantially rigid and having a first and a second end;
said first end of said proximal end portion being in fluid tight communication with said inner spiral bore;
said second end of said proximal end portion being in fluid tight communication with a source of partial vacuum for removing tissue severed from the patient by rotation of said cutting apertures.

19. A surgical tool as set forth in claim 18, wherein said inner distal end portion is substantially rigid;
said outer distal end portion being substantially rigid and having an outer distal end bore for journaling therein said inner distal end portion.

20. A surgical tool as set forth in claim 17, wherein said outer spiral is shorter in length relative to the length of said middle and inner spirals;
said inner and middle spirals defining a first ledge for the reception thereat of said inner distal end portion;
said outer spiral also defining a second ledge disposed remote from said first ledge for the reception thereat of said inner proximal end portion.

21. A surgical tool for cutting and removing tissue from a patient upon connection to a rotary power source and a source of partial vacuum, comprising:
an outer tubular member having a proximal end portion and a distal end portion,
said distal end portion of said outer tubular member defining an outer aperture;
an inner tubular member having a proximal end portion and a distal end portion;
said distal end portion of said inner tubular member defining an inner aperture;
said inner tubular member being rotatably disposed within said outer tubular member enabling said inner and outer apertures to cut the tissue of the patient upon rotation of said inner tubular member relative to said outer tubular member;
rotary coupling means for coupling said proximal end portion of said inner tubular member to the rotary power source;
flexible transmission means interconnecting said distal end portion of said inner tubular member and said proximal end portion of said inner tubular member for transmitting rotational movement of the rotary power source to said inner aperture;
said flexible transmission means including a plurality of coaxial spirally wound layers being wound in alternating opposite direction relative to each other to enable rotation of said cutting means in either a clockwise or counter-clockwise direction;
said outer tubular member being of a deformable material for enabling said outer tubular member to be selectively bent in a region adjacent said flexible transmission means of said inner tubular member for facilitating the positioning said inner and outer apertures proximate the tissue to be cut of the patient; and
fluid coupling means for coupling said proximal end portion of said inner tubular member to the source of partial vacuum for removing the tissue of the patient severed by said inner and outer apertures.

* * * * *